United States Patent
Moh et al.

(10) Patent No.: US 7,740,610 B2
(45) Date of Patent: Jun. 22, 2010

(54) SINGLE-USE SYRINGE

(75) Inventors: Jon Yaohan Moh, ChoaChu Kang Crescent (SG); Brian J. Pelkey, Rockaway, NJ (US); Julia E. Griggs, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 259 days.

(21) Appl. No.: 11/934,823

(22) Filed: Nov. 5, 2007

(65) Prior Publication Data

US 2008/0154196 A1    Jun. 26, 2008

Related U.S. Application Data

(63) Continuation of application No. 10/880,393, filed on Jun. 29, 2004, now abandoned.

(51) Int. Cl.
*A61M 5/00* (2006.01)
*A61M 5/315* (2006.01)

(52) U.S. Cl. .................................... 604/110; 604/220

(58) Field of Classification Search ................. 604/110, 604/187, 181, 209, 210, 111, 218, 199, 207, 604/208, 221, 229
See application file for complete search history.

(56) References Cited

U.S. PATENT DOCUMENTS

| | | | |
|---|---|---|---|
| 3,093,134 A | 6/1963 | Roehr | |
| 3,119,391 A | 1/1964 | Harrison | |
| 3,470,604 A | 10/1969 | Zenick | |
| 3,540,447 A | 11/1970 | Howe | |
| 4,367,738 A | 1/1983 | Legendre et al. | |
| 4,386,606 A | 6/1983 | Tretinyak et al. | |
| 4,648,873 A | 3/1987 | Robinson | |
| 4,731,068 A | 3/1988 | Hesse | |
| 4,758,232 A | 7/1988 | Chak | |
| 4,781,683 A | 11/1988 | Wozniak et al. | |
| 4,781,684 A | 11/1988 | Trenner | |
| 4,790,829 A | 12/1988 | Bowden et al. | |
| 4,826,483 A | 5/1989 | Molnar, IV | |

(Continued)

FOREIGN PATENT DOCUMENTS

EP    0037920 A1    10/1981

(Continued)

OTHER PUBLICATIONS

ISR From PCT/US05/22427, Oct. 18, 2005, 3 pgs.

(Continued)

*Primary Examiner*—Kevin C Sirmons
*Assistant Examiner*—Catherine N Witczak
(74) *Attorney, Agent, or Firm*—Diehl Servilla LLC

(57) ABSTRACT

An operable single-use syringe includes a barrel having an inside surface defining a chamber for retaining fluid and an open proximal end. A plunger rod having an elongate body portion and a stopper at its distal end slidably positioned in fluid-tight engagement in the barrel. A locking element is positioned in the barrel between the plunger rod and the inside surface of the barrel. The locking element has a base and two leg members projecting therefrom that are positioned in longitudinal grooves in the plunger rod. The locking element only moves distally in the barrel and prevents re-use of the syringe after its contents have been discharged.

23 Claims, 18 Drawing Sheets

U.S. PATENT DOCUMENTS

| | | |
|---|---|---|
| 4,838,877 A | 6/1989 | Massau |
| 4,840,616 A | 6/1989 | Banks |
| 4,883,483 A | 11/1989 | Lindmayer |
| 4,919,652 A | 4/1990 | Alter et al. |
| 4,961,728 A | 10/1990 | Kosinski |
| 4,973,310 A | 11/1990 | Kosinski |
| 4,978,339 A | 12/1990 | Labouze et al. |
| 5,000,737 A | 3/1991 | Free et al. |
| 5,147,328 A | 9/1992 | Dragosits et al. |
| 5,205,825 A | 4/1993 | Allison et al. |
| 5,215,536 A | 6/1993 | Lampropoulos et al. |
| 5,222,942 A | 6/1993 | Bader |
| 5,250,030 A | 10/1993 | Corsich |
| 5,364,387 A | 11/1994 | Sweeney |
| 5,411,499 A | 5/1995 | Dudar et al. |
| 5,445,618 A | 8/1995 | Adobbati |
| 5,733,261 A | 3/1998 | Obong |
| 5,814,017 A | 9/1998 | Kashmer |
| D405,882 S | 2/1999 | Yale |
| 5,928,215 A | 7/1999 | Caizza et al. |
| 5,989,219 A * | 11/1999 | Villas et al. .................. 604/110 |
| 6,217,550 B1 | 4/2001 | Capes |
| 6,361,524 B1 | 3/2002 | Odell et al. |
| 6,494,863 B1 | 12/2002 | Shaw et al. |
| 6,533,756 B2 | 3/2003 | Schoenfeld et al. |
| 6,991,618 B2 | 1/2006 | Lau et al. |
| 2006/0167409 A1 | 7/2006 | Pelkey et al. |

FOREIGN PATENT DOCUMENTS

| | | |
|---|---|---|
| EP | 0047042 A2 | 3/1982 |
| EP | 1123713 A1 | 8/2001 |
| WO | 89/10766 A | 11/1989 |
| WO | 2004/028604 A | 4/2004 |

OTHER PUBLICATIONS

Written Opinion From, PCT/US05/22427, Oct. 18, 2005, 5 pgs.

* cited by examiner

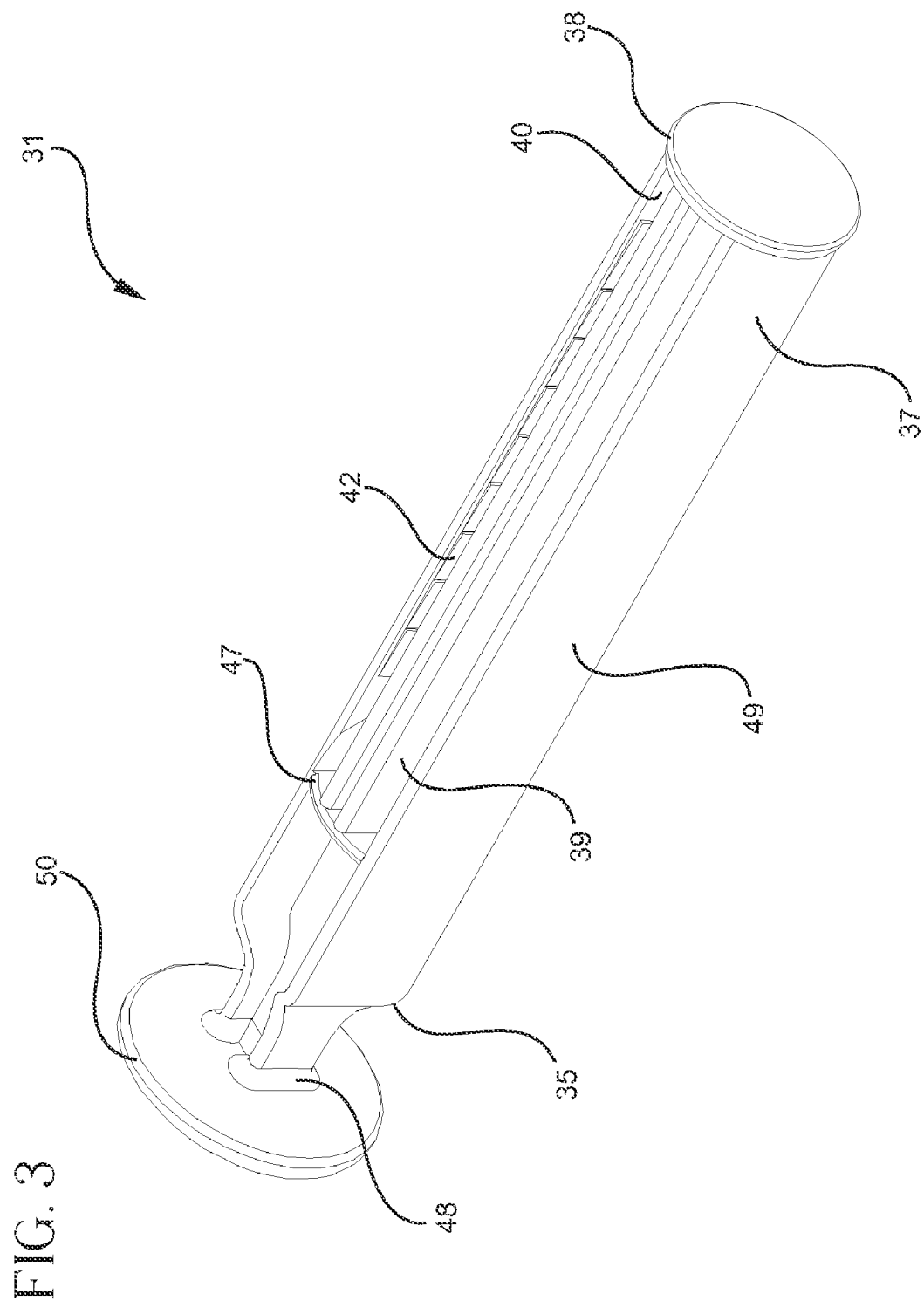

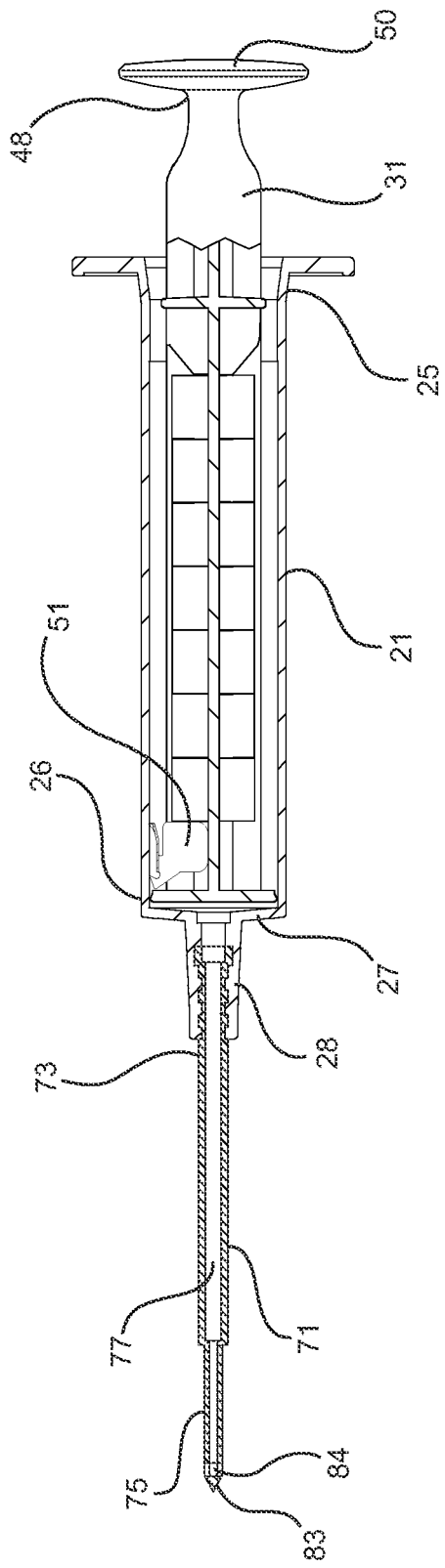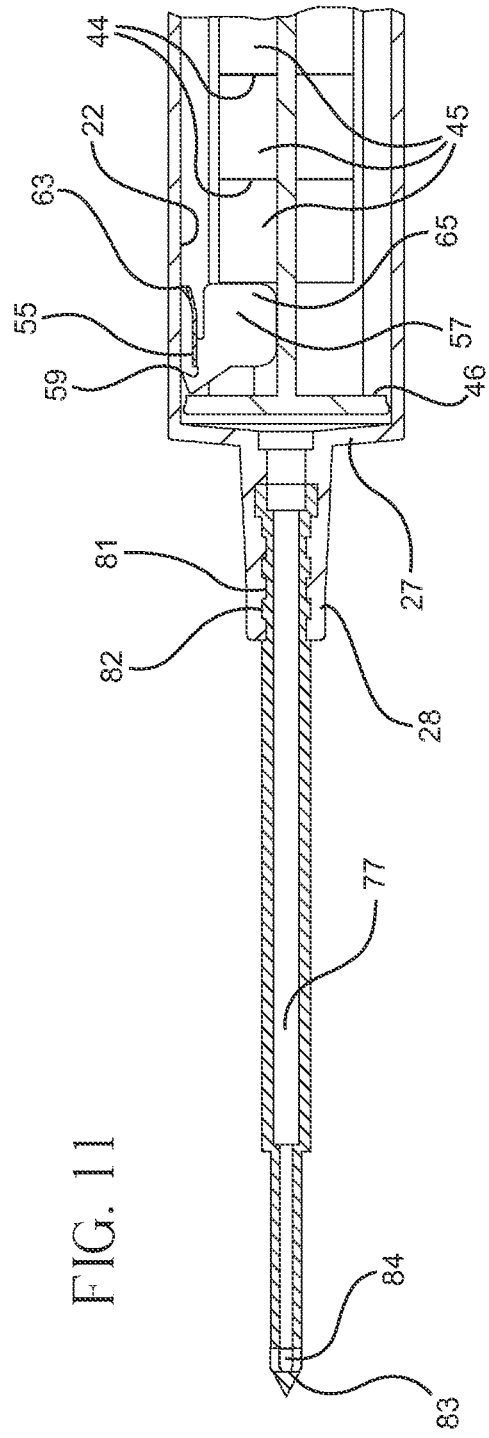
FIG. 10
FIG. 11

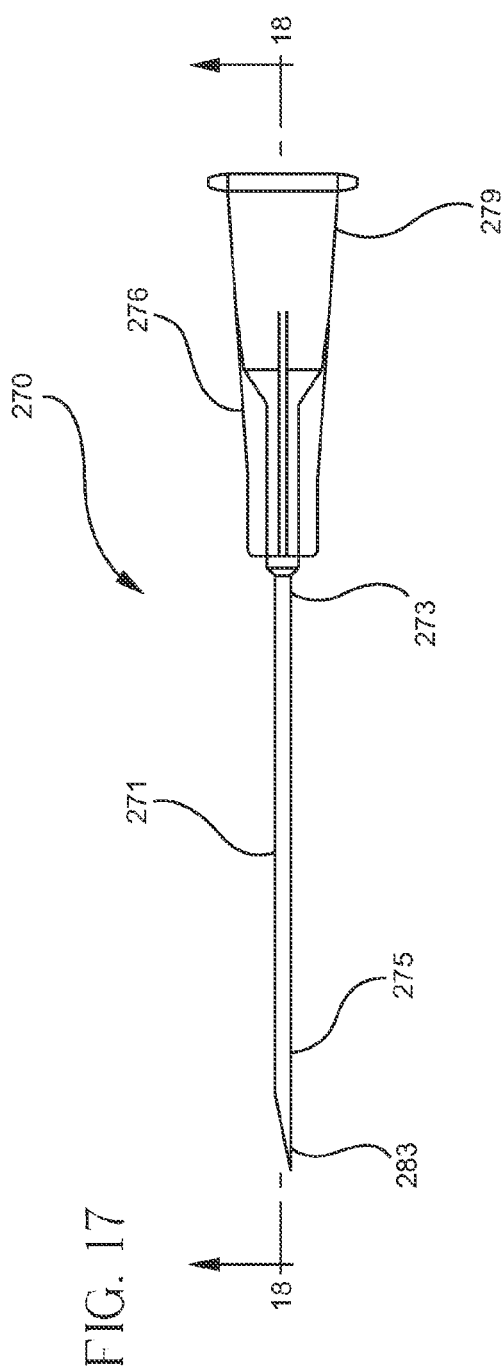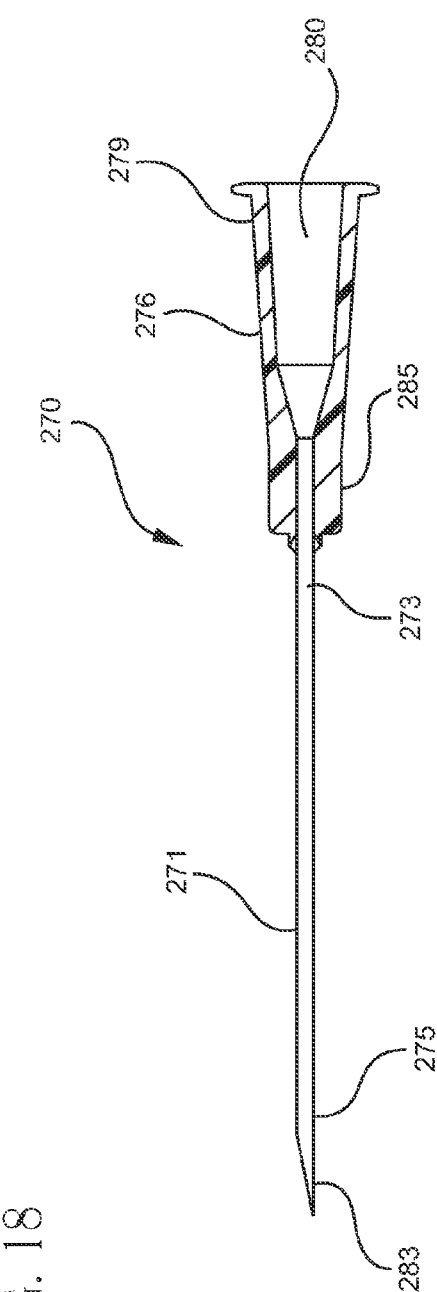
FIG. 17
FIG. 18

SINGLE-USE SYRINGE

RELATED APPLICATIONS

This application is a continuation of U.S. application Ser. No. 10/880,393 filed Jun. 29, 2004.

BACKGROUND OF THE INVENTION

The present invention relates to syringe assemblies and particularly to syringe assemblies having an automatic disabling mechanism.

Throughout the world the multiple use of hypodermic syringe products which are intended for single-use only, is instrumental in drug abuse and in the transfer of contagious diseases. Intravenous drug users who routinely share and re-use syringes are a high-risk group with respect to the AIDS virus. Also, the effects of multiple use are a major concern in some countries where repeated use of syringe products during mass immunization programs may be responsible for the spread of many diseases. Re-use of single-use hypodermic syringe assemblies is also instrumental in the spread of drug abuse even in the absence of infection or disease.

Many attempts have been made to remedy this problem. Most notable are early contributions which relies on a specific act to destroy the syringe after use either by using a destructive device or providing syringe assembly with frangible zones so that the syringe could be rendered inoperable by the application of force. Other attempts involve the inclusion of structure which would allow the destruction or defeating of the syringe function by a conscious act of the syringe user. Although many of these devices work quite well, they require the specific intent of the user followed by the actual act to destroy or render the syringe inoperable. These devices are not effective with a user having the specific intent to re-use the hypodermic syringe. Accordingly, there was a need for a single-use hypodermic syringe which after use will become inoperable or incapable of further use automatically without any additional act on the part of the user. The automatic function is much harder to provide because the means for rendering the syringe inoperable must not prevent its filling or use under normal conditions.

Single-use syringes which automatically disable after injection are taught in the art. Some of these syringes contain a locking element positioned in the syringe barrel between the plunger rod and the inside surface of the barrel. In use, the syringe allows the user to draw a pre-selected amount of medication into the chamber of the barrel and deliver this medication, as through injection, into the patient. Any attempt to withdraw the plunger to use the syringe a second time will cause the locking element to embed itself into the inside surface of the barrel to prevent proximal motion of the plunger rod.

Many times a traditional multi-use syringe and needle assembly are used to reconstitute lyophilized medication. The steps for reconstitution include withdrawing sterile water from a stoppered vial or glass ampoule into the syringe barrel and then delivering this water into a stoppered vial or glass ampoule containing the lyophilized medication. The reconstituted medication is then drawn into a single-use syringe for delivery to the patient. Single-use syringes designed specifically for reconstitution and which cannot be used for injecting medication into a patient are not presently available.

Further, mass immunization programs usually take place in developing countries where resources are limited. Accordingly, sometimes with limited resources a number of people immunized can be increased if the cost of the medication and/or the syringe is reduced. It is not desirable to reduce the cost of the single-use syringe by compromising its features since those intent on re-using syringes can be very aggressive and resourceful in their attempts to disable the safety features.

Accordingly, there is always a needle for single-use syringes which are more cost-effective and more resistant to improper re-use. Further, there is a need for a single-use syringe which is only capable of reconstitution of a dried or lyophilized drug substances and not capable of injection into the human body.

SUMMARY OF THE INVENTION

An operable single-use syringe comprises a barrel having an inside surface defining a chamber for retaining fluid, an open proximal end and a distal end having a distal wall with a tip extending distally therefrom having a passageway therethrough in fluid communication with the chamber. A plunger rod includes an elongate body portion defining a longitudinal axis, a proximal end and a distal end, a stopper at the distal end is slidably positioned in fluid-tight engagement in the barrel. The stopper may be integrally formed as part of the plunger rod or be a separate base made of the same material as the plunger rod or another material such as a thermoplastic elastomer, natural rubber, synthetic rubber and the like. The body portion of the plunger rod extends outwardly from the open proximal end of the barrel and includes a compress at its distal end to facilitate movement of the plunger rod. The body portion includes two parallel longitudinal slots wherein at least one of the slots includes a plurality of axially-spaced discontinuities, the discontinuities may take various shapes such as a saw tooth or ratchet-like structure. A locking element is positioned in the barrel between the elongate body portion of the plunger rod and the inside surface of the barrel. The locking element has a proximal end, a distal end, a base and two leg segments in substantially parallel relationship extending from the base into each of the longitudinal slots. The locking element has one or more outwardly and distal end barbs and one or more outwardly and proximally directed proximal end barbs. The barbs are for engaging the inside surface of the barrel to prevent proximal motion of the locking element with respect to the barrel. The legs include at least one deflectable, proximally positioned, resisting element for engaging the discontinuities on the plunger rod for moving the locking element in a distal direction along the inside surface of the barrel when the plunger rod is advanced in an additional direction and allowing proximal motion of the plunger rod with respect to locking element for filling the chamber.

The plunger rod may also include a proximal end barrier at its proximal end for establishing the most proximal position of the locking element on the plunger rod. The proximal end barrier may be configured to block access to the locking element through the open end of the barrel. The plunger rod may also include a distal end barrier at its distal end for establishing the distal-most position of the locking element on the plunger rod.

The single-use syringe may include a deflectable proximal resisting element on each leg member of the locking element. Each of the locking slots may include a plurality of axially-spaced discontinuities. The deflectable proximal resisting elements may face outwardly away from each other to engage the plurality of spaced discontinuities in each slot which face inwardly toward each other.

The single-use syringe may be configured so that the length of the locking element is less than 20% of the distance between the proximal end barrier and the distal end barrier.

The distal end of the locking element may include a distally directed cutting edge capable of cutting into and through the stopper if excessive proximally direct force is applied to the plunger rod to overcome the locking element and remove the plunger rod from the barrel.

The single-use syringe of the present invention may also include a needle assembly including a cannula having a proximal end, a distal end and a lumen therethrough. A hub having an open proximal end including a cavity therein, a distal end joined to the proximal end of the cannula so that the lumen is in fluid communication with the cavity. The tip of the barrel engages the hub so that the lumen of the cannula is in fluid communication with the chamber of the barrel.

The single-use syringe may also include an elongate cannula made of thermoplastic material. The cannula includes an inside surface, a proximal end, a distal end and a lumen therethrough defining a longitudinal axis. The outside surface of the cannula at its proximal end has at least one discontinuity. The distal end of the cannula includes a stopper-piercing tip. The barrel is made of thermoplastic material wherein the tip of the barrel is formed in intimate contact around the proximal end of the cannula engaging the at least one discontinuity so that the lumen is in fluid communication with the chamber.

The tip of the cannula may include a closed distal end and at least one side aperture in fluid communication with the lumen. Alternatively, the tip of the cannula may include a planar surface at an obtuse angle with respect to the longitudinal axis of the cannula.

BRIEF DESCRIPTION OF THE DRAWINGS

FIG. 3 is a perspective view of the plunger rod as viewed from the distal end.

FIG. 10 is a partially cross-sectioned side-elevation view of the single-use syringe after discharge of liquid from the chamber of the barrel.

FIG. 11 is an enlarged partial side-elevation view of the syringe assembly of FIG. 10.

FIGS. 17-19 illustrate a removable needle assembly for use with the single-use syringe.

DETAILED DESCRIPTION OF THE INVENTION

Figure 1:
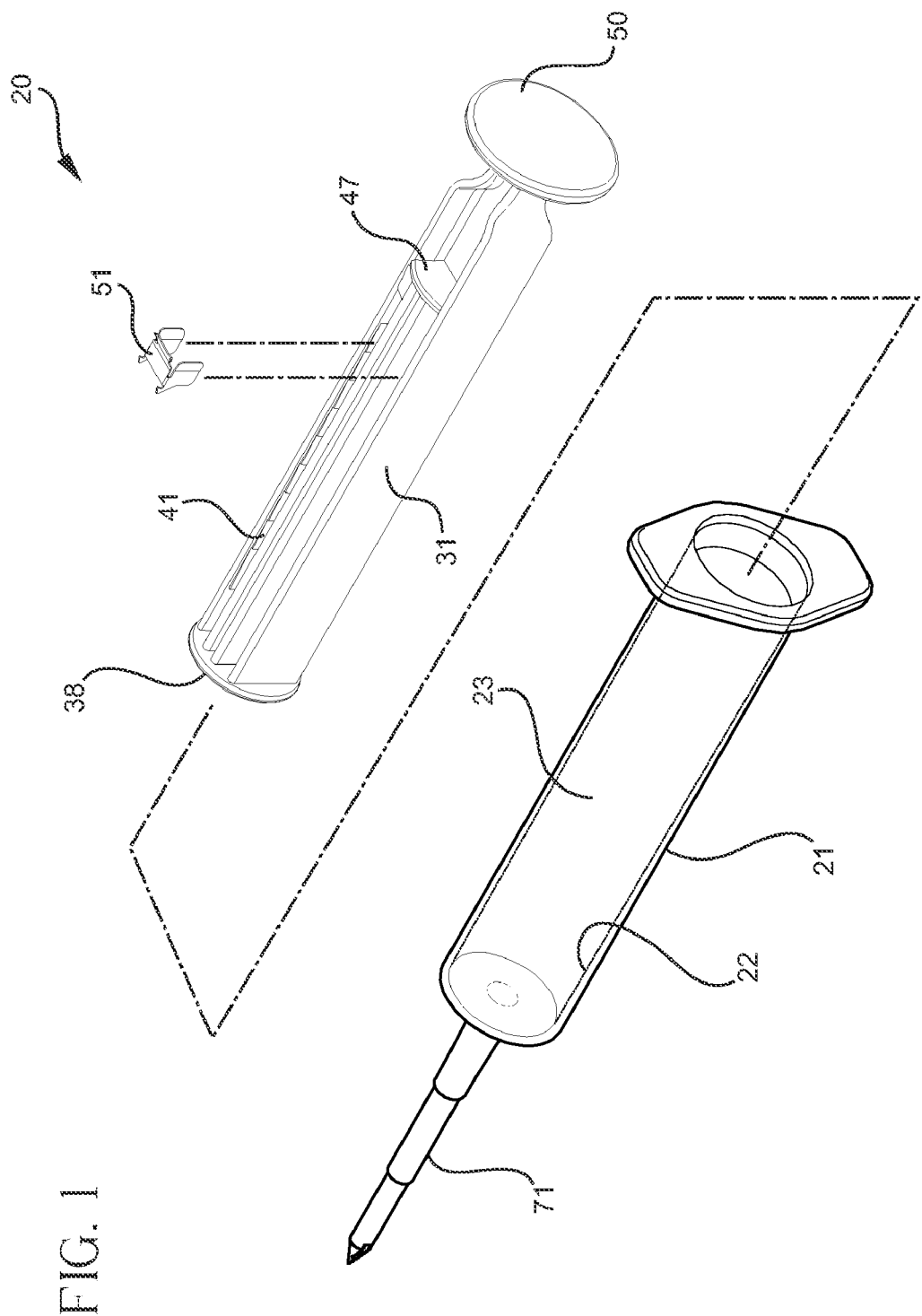
FIG. 1 is an exploded perspective view of one embodiment of the single-use syringe of the present invention.
Figure 2:
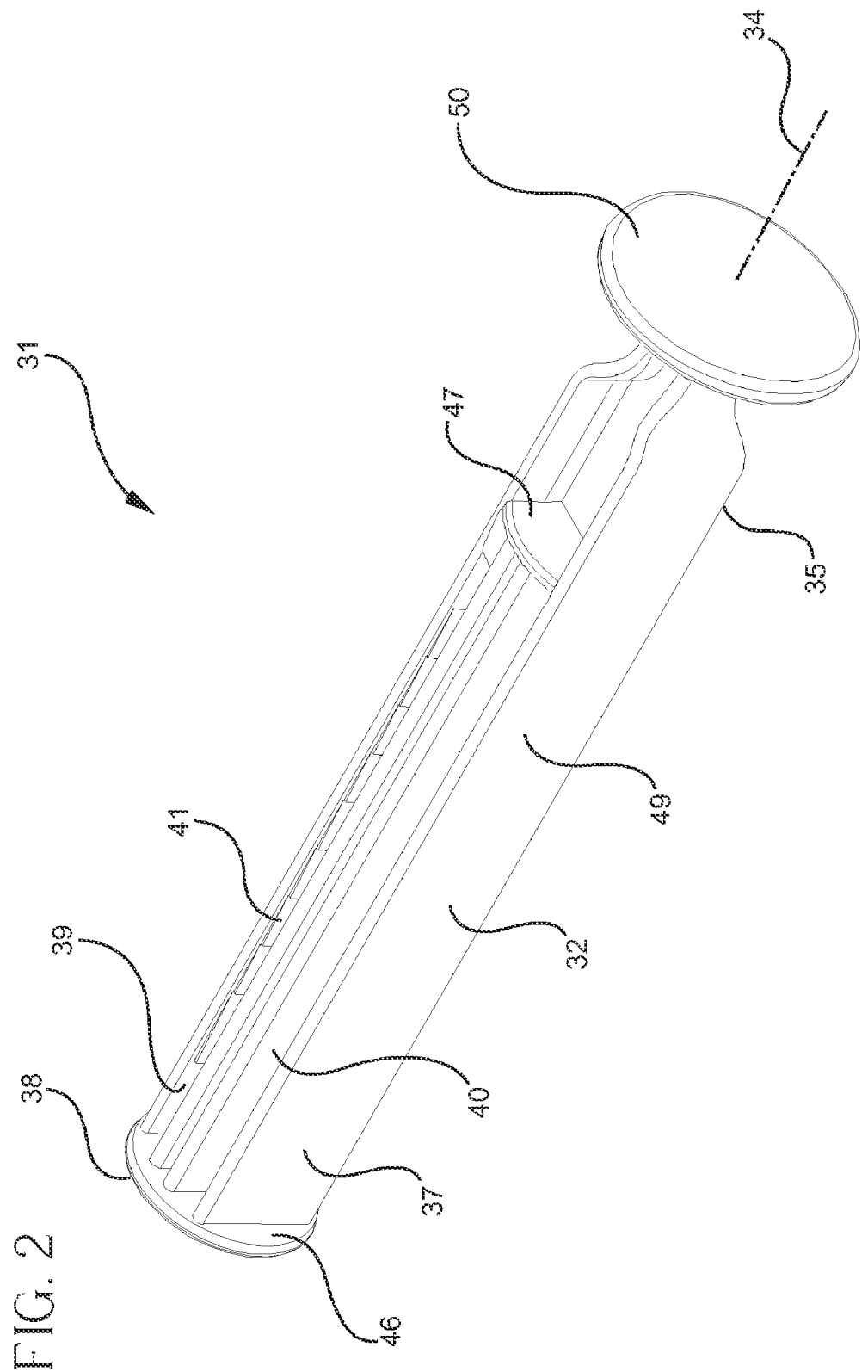
FIG. 2 is a perspective view of the plunger rod of the syringe of FIG. 1 as viewed from the proximal end.
Figure 2A:
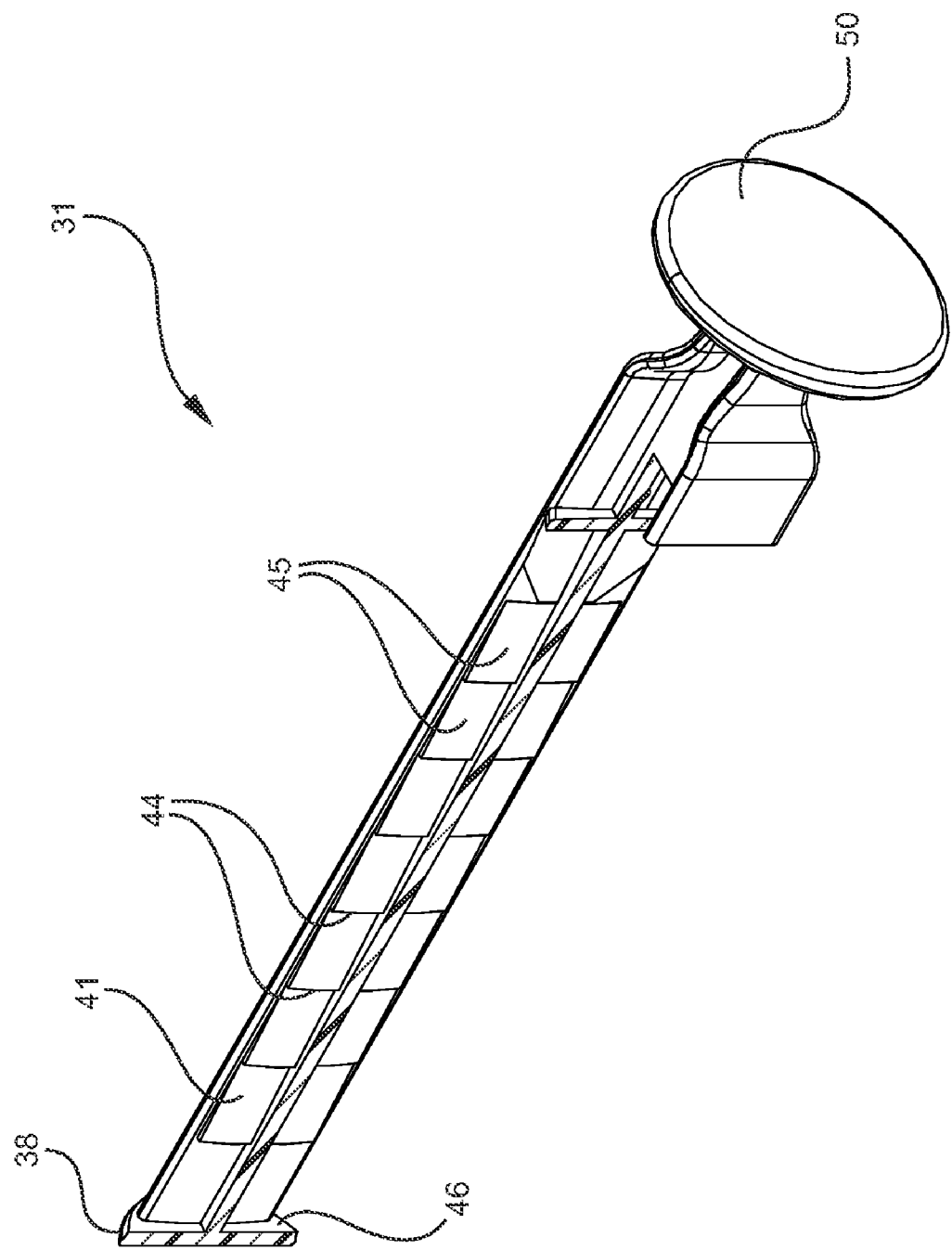
FIG. 2A is a partially cross-sectioned view of the plunger rod of FIG. 2 taken along its longitudinal axis.
Figure 3A:
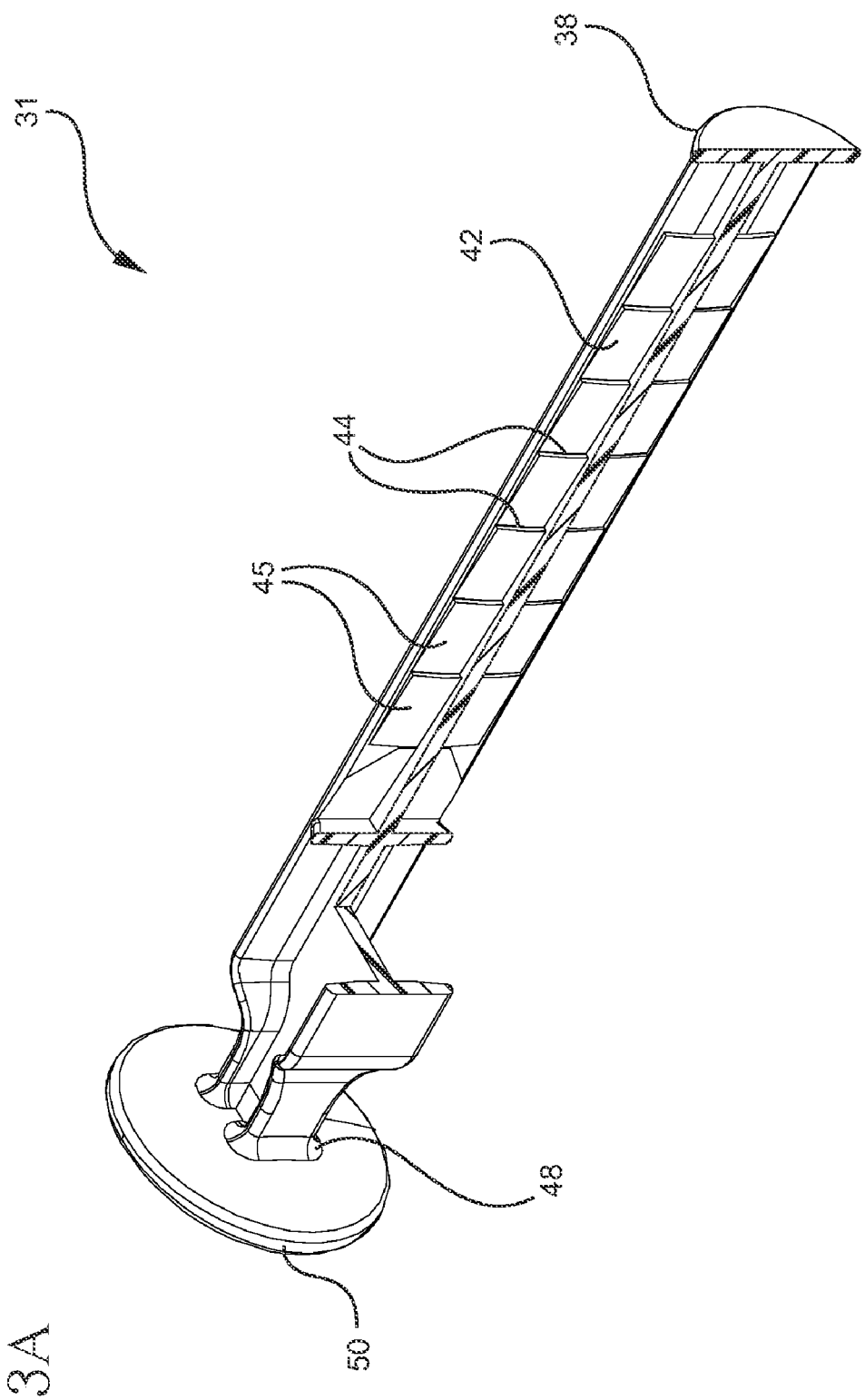
FIG. 3A is a partially cross-sectioned view of the plunger rod of FIG. 3 taken along its longitudinal axis.
Figure 4:
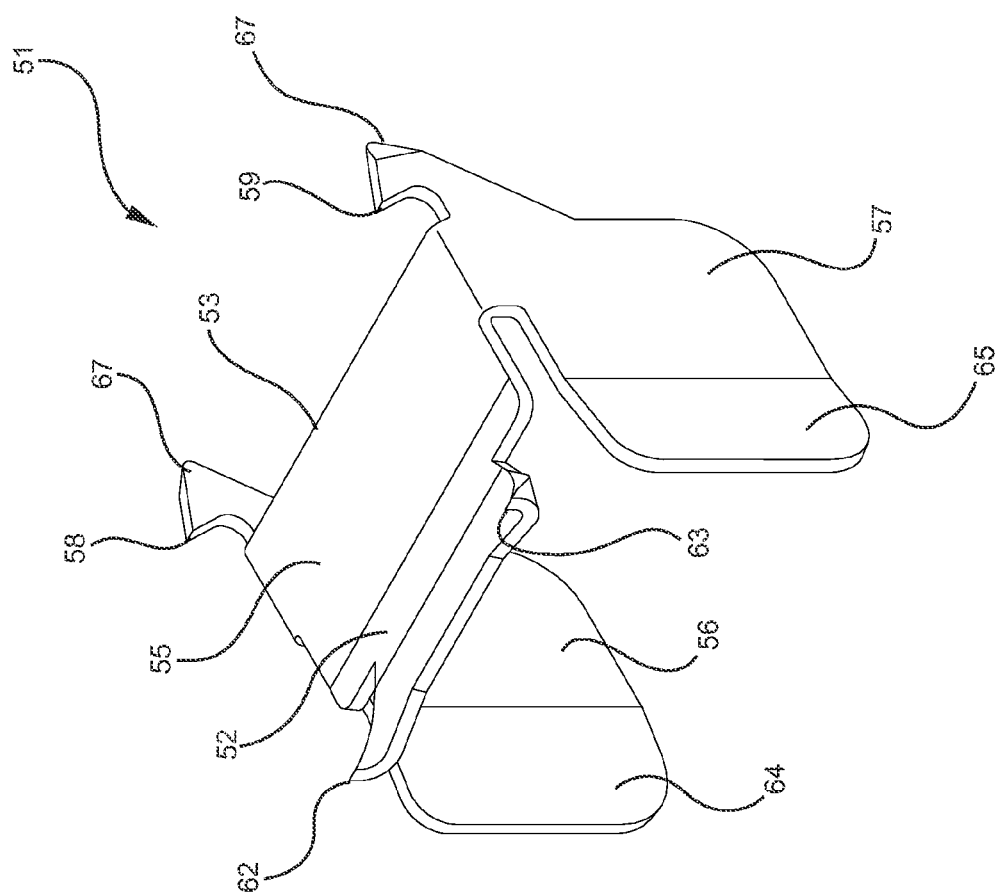
FIG. 4 is a perspective view of the locking element viewed from the proximal end.
Figure 5:
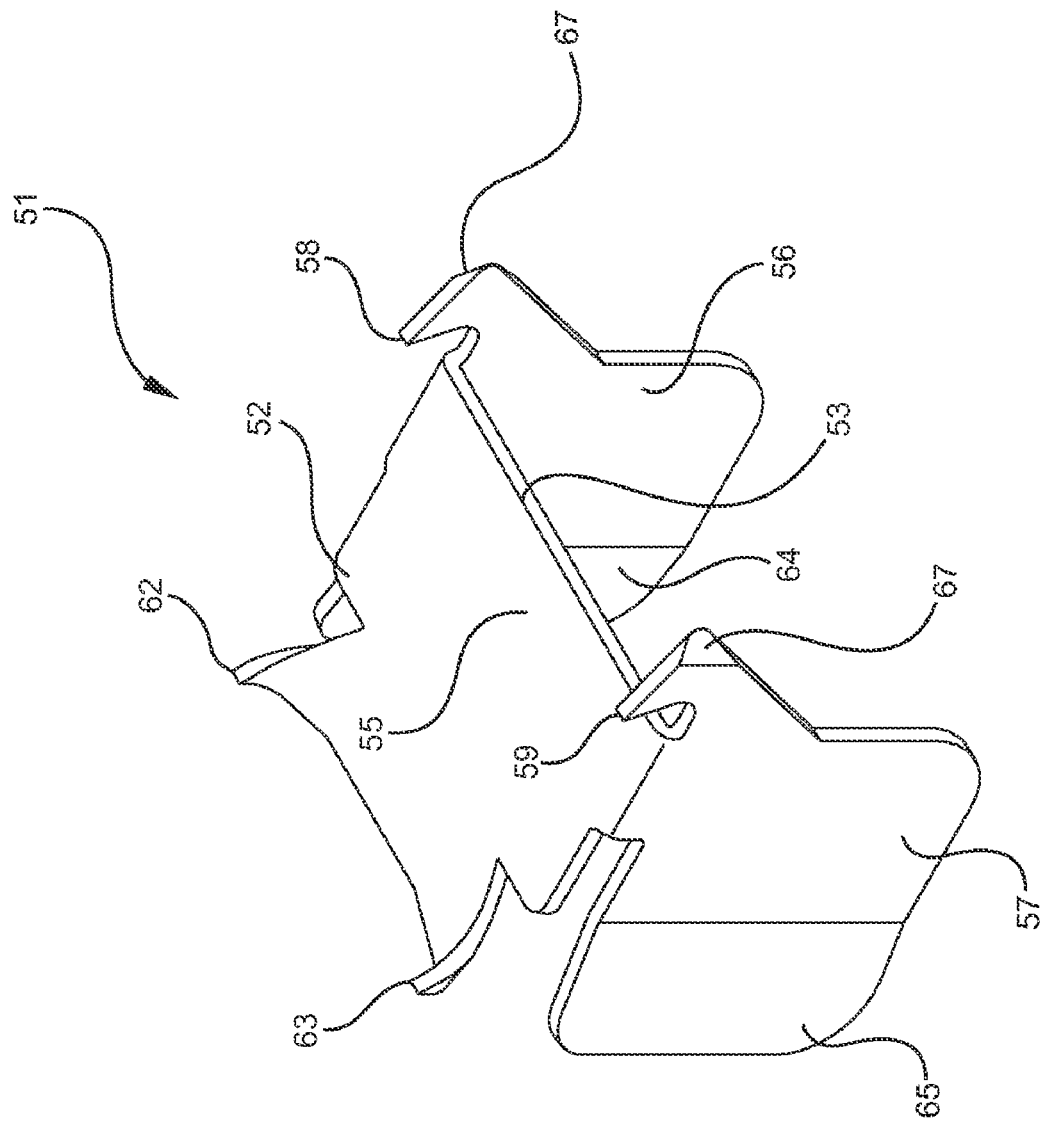
FIG. 5 is a perspective view of the locking element viewed from the distal end.

There is shown in the drawings and will be described in detail herein preferred embodiments of the invention with the understanding that the present disclosure is to be considered exemplary of the principles of the invention and is not intended to limit the invention to the embodiments illustrated. The scope of the invention will be measured by the appended claims and their equivalents.

For the purpose of the description of the present invention, the term "distal end" is intended to refer to the end furthest from the person holding the syringe, whereas the term "proximal end" is intended to refer to the end closest to the holder of the syringe.

An operable single-use syringe comprises a barrel 21 having an inside surface 22 defining a chamber 23 for retaining fluid, an open proximal end 25 and a distal end 26 having a distal wall 27 with a tip 28 extending distally therefrom having a passageway 29 therethrough in fluid communication with the chamber.

A plunger rod 31 includes an elongate body portion 32 defining a longitudinal axis 34, a proximal end 35 and a distal end 37. A stopper 38 at the distal end of the plunger rod is slidably positioned in fluid-tight engagement in the barrel. The stopper may be a separate element connected to the body portion of the plunger rod. The separate stopper may be made of thermoplastic materials, thermoplastic elastomers, natural rubber, synthetic rubber and combinations thereof. The stopper in this embodiment is integrally formed with the elongate body portion and it is made of thermoplastic material such as polyethylene. The body portion of the plunger rod extends outwardly from the open proximal end of the barrel to facilitate moving the stopper in the barrel. The body portion includes two parallel longitudinal slots 39 and 40. At least one of the slots includes a plurality of axially-spaced discontinuities such as ratchet-like teeth 41 in slot 39. In this embodiment, longitudinal slot 40 also includes axially-spaced discontinuities in the form of a ratchet-like teeth 42. The teeth include distally-facing surfaces 44 and inclined surfaces 45. As will be explained hereinafter, the axially-spaced discontinuities can take a wide variety of shapes and forms all falling within the purview of the present invention with the ratchet-like teeth being merely representative of these various possibilities.

A locking element 51 is positioned in the barrel between the elongate body portion of the plunger rod and the inside surface of the barrel. The locking element includes a proximal end 52, a distal end 53, a base 55 and leg members 56 and 57 in substantially parallel relationship extending from the base into each of the longitudinal slots in the plunger rod. A locking element has at least one outwardly and proximally directed distal end barb, and in this embodiment there are two distal end barbs 58 and 59 for engaging the inside surface of the barrel to prevent proximal motion of the locking element with respect to the barrel. The locking element also includes at least one outwardly and proximally directed proximal end barb, and in this embodiment includes proximal end barbs 62 and 63 also for engaging the inside surface of the barrel to prevent proximal motion of the locking element with respect to the barrel. There should be at least one deflectable resisting element extending from one of the leg members. In this embodiment there are two deflectable resisting elements 64 and 65 for engaging the ratchet-like teeth on the plunger rod for moving the locking element in a distal direction along the inside surface of the barrel when the plunger rod is advanced in a distal direction and allowing proximal motion of the plunger rod with respect to the locking element when filling the chamber. In this embodiment, axially-spaced discontinuities in the form of ratchet-like teeth 41 and 42 face each other while deflectable resisting elements 64 and 65 face outwardly away from each other for engaging the discontinuities. Plunger rod 31 in this embodiment is symmetric along its longitudinal axis having longitudinal slots with discontinuities on two sides. This symmetric configuration is believed to improve manufacturability by reducing the angle the plunger must be rotated to align with a locking element positioned for insertion in the longitudinal slots of the plunger rod. With this two-sided configuration the maximum angle a plunger rod must be rotated to accept a locking element is 90° versus 180° for a non-symmetrical plunger rod having only the two longitudinal slots.

In this embodiment the plunger rod includes a distal end barrier 46 at the distal end of the body portion for establishing the distal-most position of the locking element on the plunger rod. In this embodiment, the stopper and the distal end barrier are integrally formed. This embodiment also includes a proximal end barrier 47 at the proximal end of the plunger rod for establishing the most proximal position of the locking element on the plunger rod. The proximal end barrier is preferably large enough to block a substantial portion of the bore of the barrel for blocking access to the locking element through the open proximal end of the barrel. This structural feature will frustrate attempts to use small tools to defeat the locking element and improperly re-use the syringe. A proximal end barrier that is large enough to block direct visual contact with the locking element through the open proximal end of the barrel should be large enough to block access to the locking element. Also, the channel-shaped locking element is supported and shielded from tampering by relatively large sidewalls 49 on the plunger rod. Further, the substantial structure of the plunger rod surrounding the locking element supports the locking element and helps it resist attempts to overcome the locking element by improperly twisting the plunger rod because rotation of the plunger rod drives the distal and proximal end barbs into the inside surface of the barrel further enhancing the grip of the locking element to the barrel. Also, connection 48 holding thumb press 50 on proximal end of elongate body portion 32 can be made frangible by structure and/or material so that excessive twisting or tension forces applied to the thumb press will cause it to disconnect from the remainder of the plunger rod to provide further resistance to improper tampering. These structural and functional improvements are important aspects of the present invention.

Figure 6:
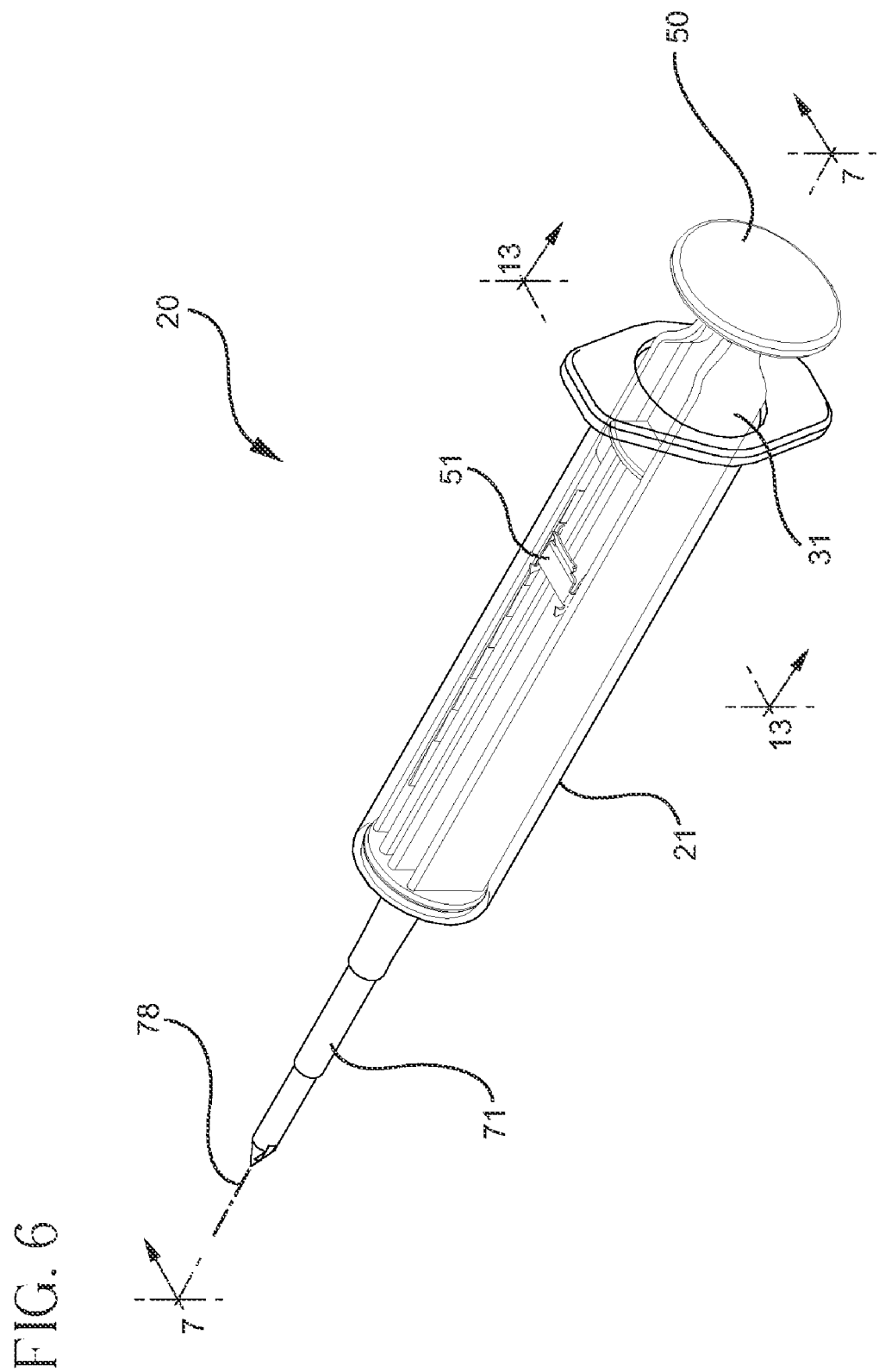
FIG. 6 is a perspective view of the single-use syringe before use.
Figure 7:
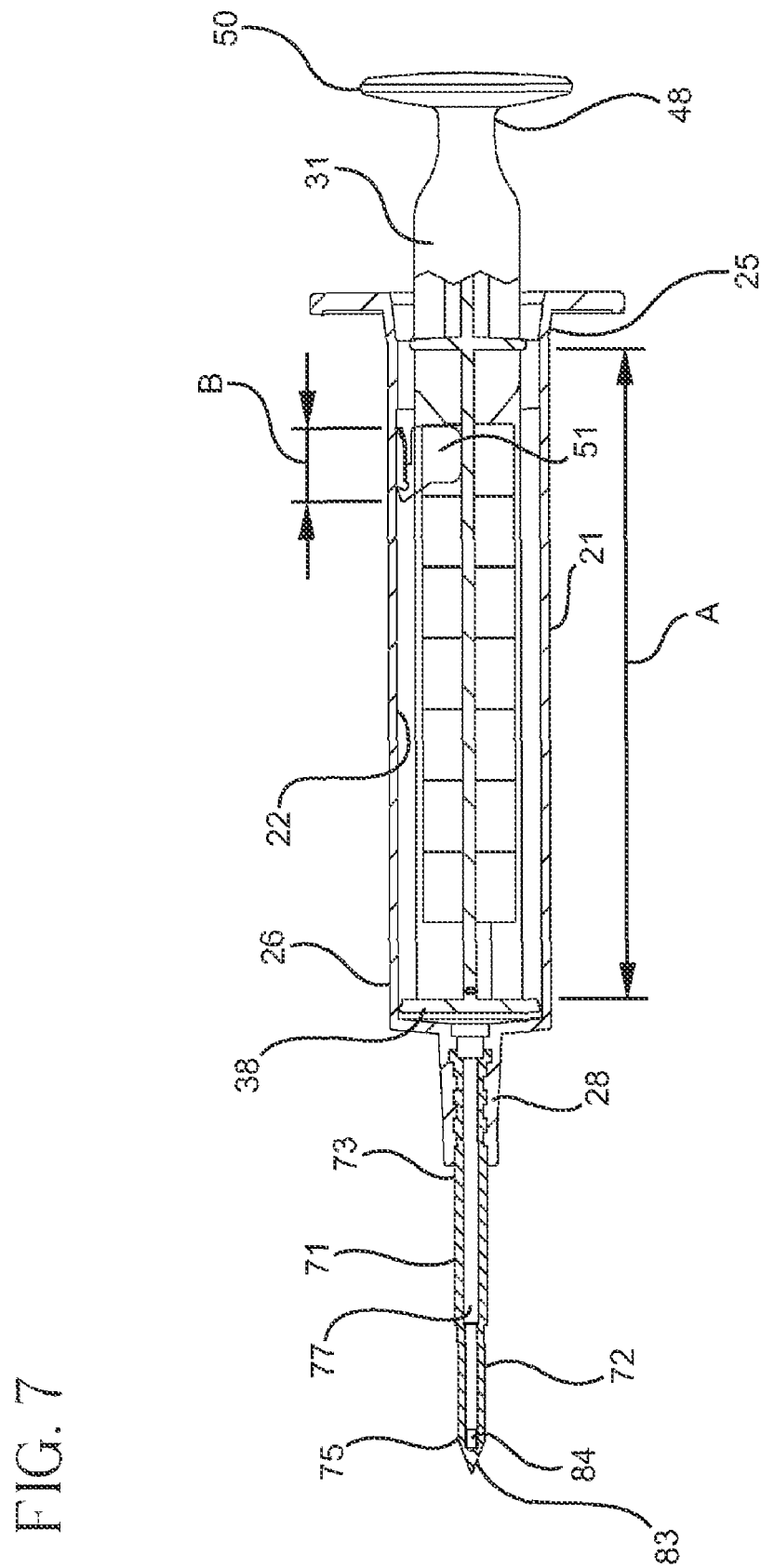
FIG. 7 is an enlarged partially cross-sectioned side-elevation view of the single-use syringe of FIG. 6.
Figure 8:
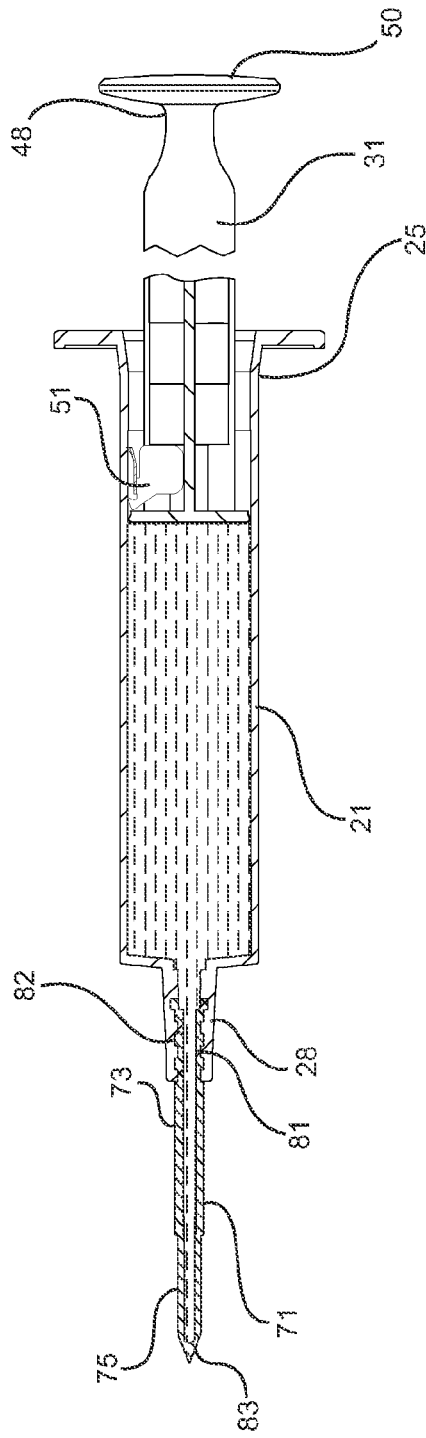
FIG. 8 is a partially cross-sectioned side-elevation view of the single-use syringe after liquid has been drawn into the barrel chamber.

As best seen in FIGS. 7 and 8 the maximum stroke of the plunger rod, and therefore the maximum volume the syringe can deliver, is a function of distance A between distal end barrier 46 and proximal end barrier 47 minus the axial length B of the locking element. The channel-shaped configuration of locking element 51 and the support provided by the structure surrounding the longitudinal slots in the plunger rod allow locking element length B to be less than some other prior art locking elements while still being strong enough to prevent re-use. Accordingly, all things being equal, short locking element 51 will allow more volume to be delivered from the syringe. The locking element and plunger rod of the present invention has been configured to fit an available 5 ml syringe barrel and still allow the delivery of a full 5 ml dose. Some prior art devices yield less than half the volume that the syringe barrel is capable of delivering in a non-single-use configuration. Using the structure of the present invention results in a more cost-effective single-use syringe structure therefore making more syringes available for mass immunization in a fixed budget program. It is preferred that axial length B of the locking element be less than 20% of the distance A between the distal end barrier and the proximal end barrier. As shown in FIGS. 1, 6 and 7, the locking element is positioned in its distal-most position allowing for the maximum delivery volume. However, the delivery volume for the syringe can be reduced by initially positioning the locking element distally from the proximal barrier.

As will be explained in more detail hereinafter, the single-use syringe of the present invention can be used in conjunction with a removable needle assembly, a permanently attached needle for injection or a plastic cannula suitable for reconstitution and not for human injection. In this embodiment the single-use syringe is illustrated with a thermoplastic cannula to function as a single-use reconstitution syringe assembly. In particular, cannula 71 preferably made of thermoplastic material, includes an outside surface 72, a proximal end 73, a distal end 75 and a lumen 77 therethrough defining a longitudinal axis 78. Outside surface 72 at the proximal end of the cannula includes at least one discontinuity. In this embodiment the at least one discontinuity includes annular grooves 81 and annular projections 82.

The distal end of the cannula includes piercing tip 83. The piercing tip is much less sharp than the tip of a metal hypodermic needle, but still sharp enough to pierce the elastomeric stopper of a medication vial. The cannula at the distal end is much larger than a hypodermic needle intended for injection. In this embodiment, the distal end of the cannula has an outside diameter of at least 2 mm (0.08 inch). The combination of the large diameter distal end of the cannula and the relatively blunt piercing tip results in a cannula that is unsuitable for injection and much less likely to cause accidental skin piercing which could result in injury or transfer of disease. The term "piercing tip" as used herein is intended to encompass the tips of larger than injection needle diameter being configured to piece elastomeric septums of injection vials and not human skin under normal use. The cannula includes the proximal portion having a diameter larger than the diameter of the distal portion. The diameter of the proximal end is equal or greater than about 2.5 mm (0.1 inch). The increased proximal portion diameter substantially strengthens the cannula when bending forces are applied without, as will be explained hereinafter, interfering with the ability to function properly.

In this embodiment, the distal end of the cannula at the piercing tip is closed and includes at least one side aperture 84 in fluid communication with lumen 77.

Figure 16:
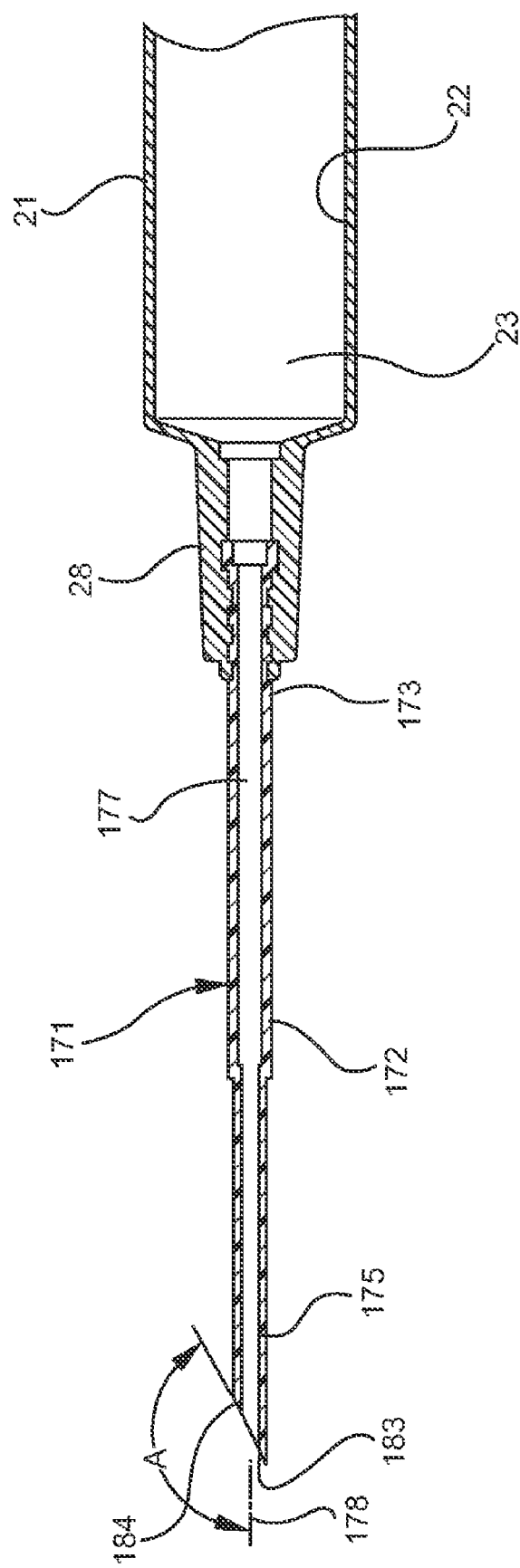
FIG. 16 is a side-elevational cross-sectional view of the distal end of the single-use syringe barrel showing an alternative cannula tip.

Piercing tips within the purview of the present invention can include other configurations. FIG. 16 illustrates an alternative embodiment wherein cannula 171 includes an outside surface 172, a proximal end 173, a distal end 175 and a lumen 177 therethrough defining longitudinal axis 178. A piercing tip 183 at the distal end of the cannula has an outside diameter of at least 2 mm (0.08 inch). The piercing tip has a generally planar surface 184 positioned at an obtuse angle A with respect to longitudinal axis 128.

The syringe barrel is made of thermoplastic material and tip 28 is formed in intimate contact around proximal end 73 of the cannula engaging the annular grooves and projections so that lumen 77 is in fluid communication with chamber 23. Cannula 71 preferably projects distally from the distal wall of the barrel for a distance of at least 23 mm (0.9 inch). In this preferred embodiment cannula 21 extends at least 23 mm (0.9 inch) beyond the distal end of tip 28. The thermoplastic material of the cannula has a higher flexural modulus than the thermoplastic material of the barrel. The flexural modulus of the cannula material is at least 50% higher than the flexural modulus of the barrel material. In this embodiment, the barrel is preferably formed of polypropylene and the cannula is preferably made of polycarbonate.

In the prior art, short hypodermic needle assemblies and short cannula-like spikes are used to withdraw liquid from a stoppered vial. Because these elements are removable, the syringe assembly used in the procedure can be subsequently improperly used with a needle for injecting substances into a person. In the case of a hypodermic needle being used to access the vial, the needle can also be improperly used if not properly disposed. The single-use syringe of the present embodiment eliminates these problems by providing an integral cannula and syringe barrel wherein the cannula has a large piercing tip not suitable for injecting substances into people. Further, it is easier to dispose of since it does not have any metal components. However, an integrally formed barrel and cannula having a short cannula would not be suitable for drawing liquid from a glass ampoule since the ampoule cannot be inverted without spilling the liquid and the cannula must be long enough to reach to the bottom of the ampoule. For these applications, a long hypodermic needle is used. This combination results in the same problems as having a potentially re-usable needle assembly and syringe barrel reusable for human injection as previously described. Further, a long plastic cannula made of commonly used plastics for these applications, such as polypropylene, may bend or become damaged if it were used in an attempt to pierce a stoppered vial. This is due to the long length of the cannula which renders it generally undesirable for piecing vials. It is an important aspect of the present invention that all of the above-mentioned problems are overcome by providing a syringe assembly having permanently attached cannula with a relatively large piecing tip which is not suitable for human injection. Further, the cannula is long enough to access vials yet strong enough to piece vial stoppers to effectively withdraw liquid from a vial. Also, disposal is simplified because there are no metal components in the syringe assembly. The issue of strength is addressed by forming the cannula of a substantially more rigid material than the barrel. Also when the stopper is a rigid element, as in the preferred embodiment, the barrel must be flexible enough to provide a fluid-tight seal around the periphery of the stopper. The more rigid material used in the cannula could not be used in the barrel because the barrel would not have the necessary flexibility to provide an efficacious seal around the stopper and still allow the plunger rod to move with respect to the barrel when reasonable forces are applied. The syringe assembly of the present invention overcomes the deficiencies of the prior art by providing a reconstitution syringe having a rigid plastic cannula with a tip not suitable for human injection which can adequately access stoppered vials and glass ampoules to reconstitute medication and subsequently to be easily destroyed and not be a danger for drug is-use.

Figure 9:
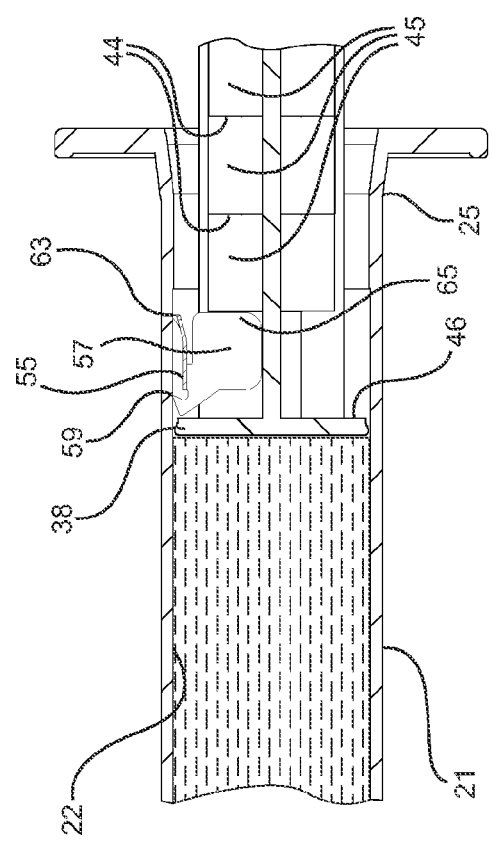
FIG. 9 is an enlarged partial side-elevation view of the syringe assembly of FIG. 8.

Single-use syringe 20 is assembled by placing locking element 51 on the plunger rod so that leg members 56 and 57 are in longitudinal slots 39 and 40 and then plunger rod 31 with locking element 51 is inserted in the proximal end of the barrel. The position of the locking element on the plunger rod when the syringe is assembled determines the maximum dose the syringe assembly can deliver. Single-use syringe 20 as assembled and ready to use is illustrated in FIGS. 6 and 7. Deflectable resilient elements 64 and 65 on the locking element work in conjunction with ratchet-like teeth 43 to allow the plunger rod to move in the proximal direction with respect to the locking element to draw liquid into the barrel as illustrated in FIGS. 8 and 9. The locking element cannot move in a proximal direction due to the engagement of distal end barbs 58 and 59 and proximal end barbs 62 and 63 with the inside surface of the barrel. However, the ratchet-like teeth working in conjunction with the deflectable resisting elements allow the plunger to move proximally with respect to the locking element to fill a syringe barrel. To discharge liquid from the chamber of the barrel, force is applied to the thumb press of the plunger rod to move the plunger rod in a distal direction with respect to the barrel. As plunger rod 31 moves distally in barrel 21 the interaction of the ratchet-like teeth and deflectable resilient elements on the locking element cause the locking element to move distally in the barrel along with the plunger rod until the stopper contacts distal wall 27 of the barrel. At this point the plunger rod can no longer move distally within the barrel and it can no longer move proximally within the barrel because the distal end barbs 58 and 59 and the proximal end barbs 62 and 63 are engaging the barrel and preventing withdrawal of the plunger rod from the barrel.

Figure 12:
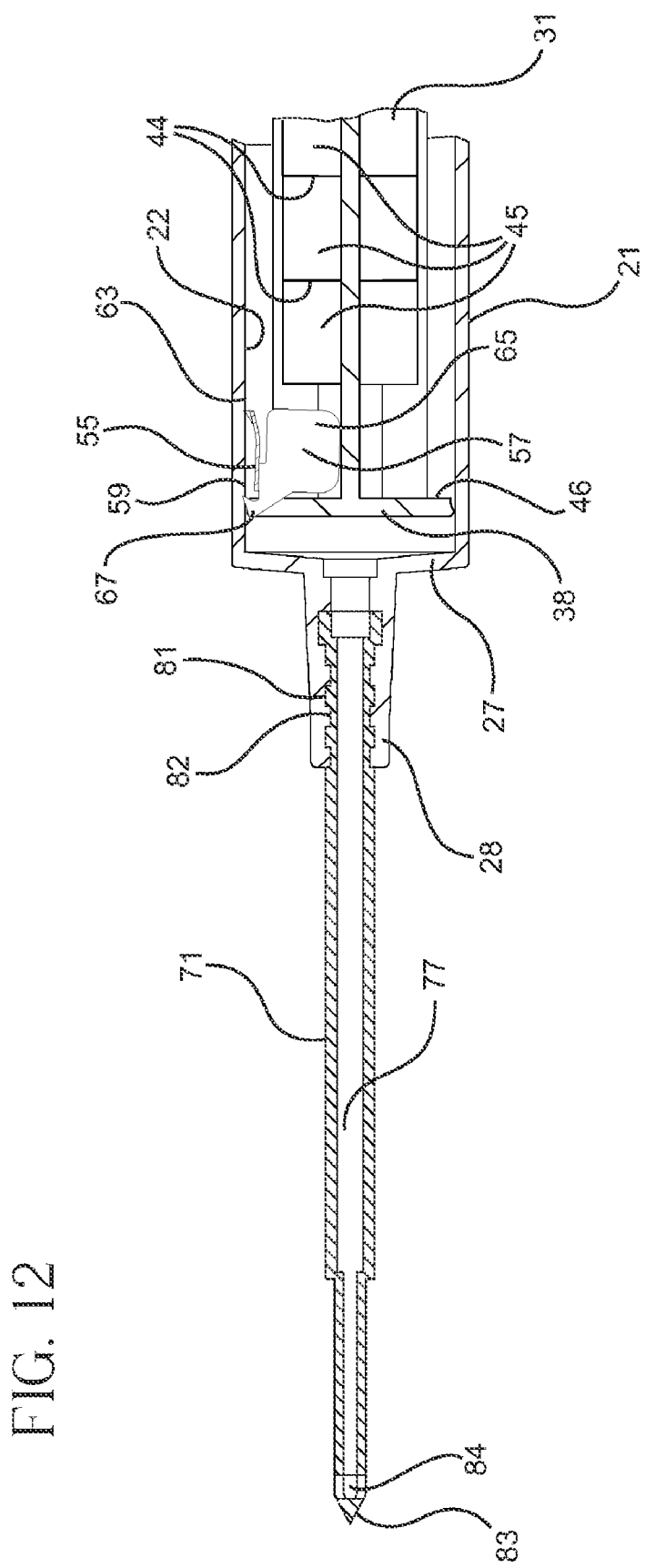
FIG. 12 is an enlarged partially cross-sectioned view, similar to FIG. 11, showing the locking element cutting through the stopper.
Figure 13:
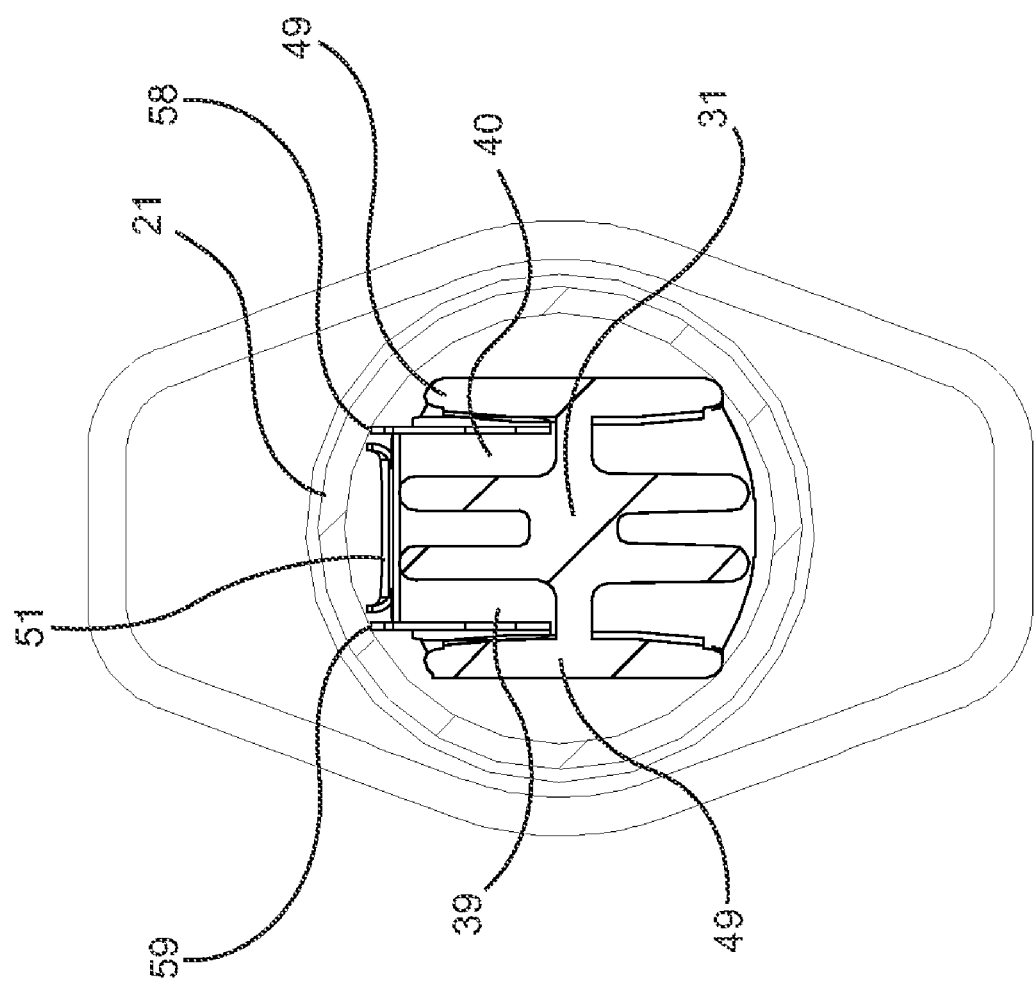
FIG. 13 is an enlarged cross-sectional view of the syringe of FIG. 6 taken along line 13-13.

Locking element 51 further includes distally directed cutting edge 67 which provides further protection against improper re-use of the single-use syringe. By applying excessive proximally-directed force to the plunger rod, as illustrated in FIG. 12, the stopper will be pulled proximally with respect to the cutting edge causing the cutting edge to cut through the stopper or to severely damage the stopper so that the stopper is cut and disfigured and can no longer function effectively to discharge liquid from the barrel.

Figure 14:
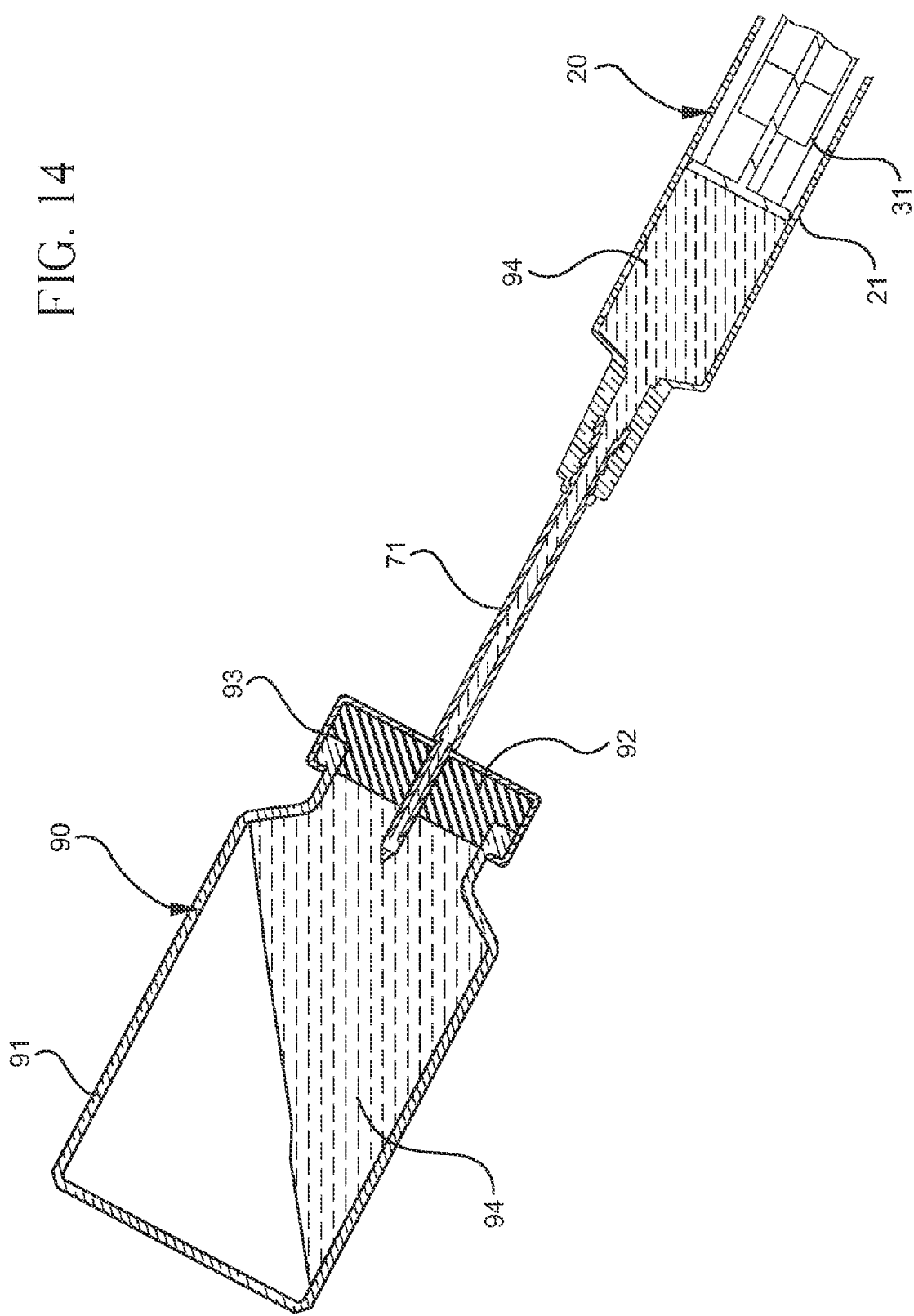
FIG. 14 is a partially cross-sectioned side-elevation view illustrating the single-use syringe being used to remove sterile liquid from a stoppered vial.

The present embodiment of the single-use syringe having a thermoplastic cannula with a piercing tip can be used to reconstitute medications wherein the liquid component is contained in a stoppered vial. As illustrated in FIG. 14, stoppered vial 90 includes a vial 91, a pierceable stopper 92, a sheet metal closure 93 for holding the stopper in place on the vial and a quantity of sterile liquid 94. The liquid is drawn into the syringe using known clinically accepted methods which include piercing the stopper of the vial with piercing tip 83 of cannula 71 and moving the plunger in a proximal direction with respect to the barrel to draw liquid into the chamber of the barrel while the vial is inverted so that the short length of cannula can access all of the liquid in the vial. The plunger can draw liquid into the barrel until distal end barrier 46 contacts locking element 51. Syringe 20 with integral cannula 71 is then withdrawn from the stoppered vial and used to transfer liquid into the dried or lyophilized medication, such as vaccine, for subsequent injection into the patient. The vaccine may also be contained in a stoppered vial. If so, the integral cannula of the syringe assembly can again be used to pierce the stopper and force the water into the medication containing vial for subsequent injection into a patient.

Figure 15:
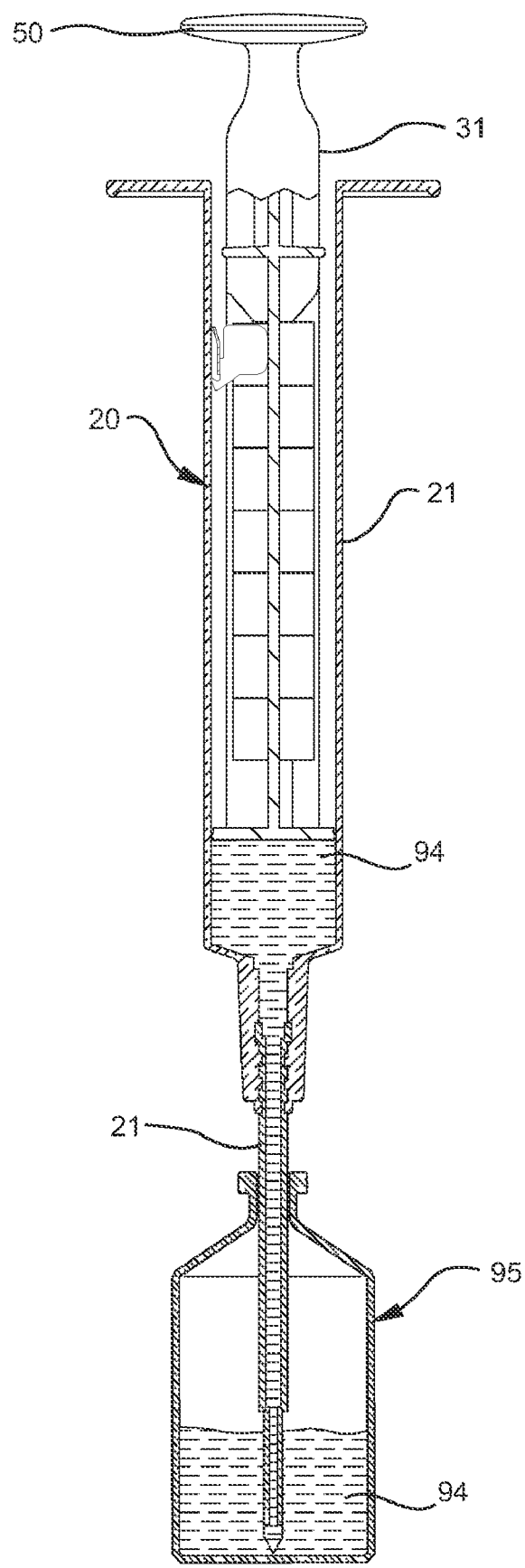
FIG. 15 is a partially cross-sectioned side-elevation view showing the single-use syringe being used to withdraw sterile liquid from a glass ampoule.

FIG. 15 illustrates syringe assembly 20 being used to withdraw sterile liquid from a glass ampoule 95 containing sterile liquid 94. For this application, the cannula must be small enough to enter the severed neck of the ampoule and long enough to access sterile liquid 94 at the bottom of the ampoule. It is anticipated that a cannula with an effective length of 23 mm (0.9 inch) to 38 mm (1.5 inch) will be able to work with the majority of ampoules believed to be available. It is preferred that the effective length be measured from the distal end of the barrel tip to the distal end of the cannula since it is anticipated that a barrel tip of adequate strength will be much larger than the cannula and not suitable to enter some ampoules. However, if the barrel tip is small enough to fit into the ampoule, the effective length can be measured from the distal wall of the barrel.

The flexural modulus of the cannula material, measured in units Mpa is at least 50% greater than the flexural modulus of the barrel material. Preferred materials for the barrel and the cannula are polypropylene and polycarbonate respectively. Polycarbonate, having a flexural modulus of about 2275 Mpa gives the cannula the substantial strength it needs to function properly and still be long enough to access the full depth of an ampoule and the polypropylene, having a flexural modulus of about 1100 Mpa, provides a relatively flexible, less rigid, barrel that will provide an adequate seal for a thermoplastic stopper made of material such as polyethylene. Also, the shrinkage rate of polypropylene in the molding process is greater than the shrinkage rate of polycarbonate so that as the molded polypropylene which surrounds the proximal end of the polycarbonate cannula solidifies the barrel tip will shrink tightly around the polycarbonate needle to hold it even with more force than if the materials had similar shrinkage rates. Accordingly, even if the polycarbonate cannula is still in the process of solidifying injection molding of the barrel over the cannula is possible.

Figure 19:
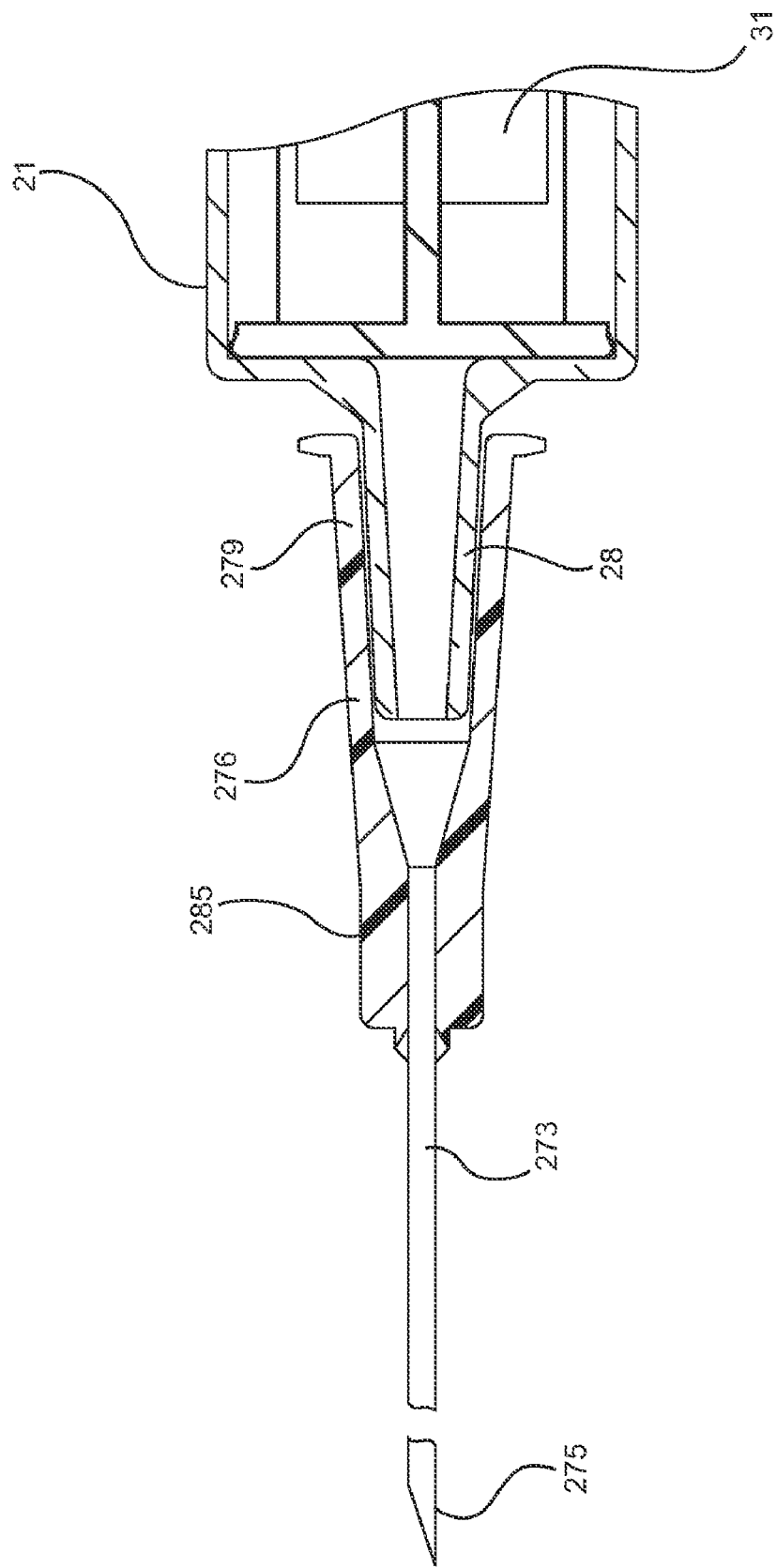

Referring to FIGS. 17-19, the single-use syringe of the present invention can also be used with a removable needle assembly for reconstitution or injection and the like. Needle assembly 270 includes a cannula 271 having a proximal end 273, a distal end 275 and a lumen 277 therethrough, and a hub 276 having an open proximal end 279 including a cavity 280 therein. A distal end 285 of the hub is joined to the proximal end of the cannula so that the lumen of the cannula is in fluid communication with the cavity. Tip 28 of the barrel removably engages the hub of the needle assembly so that the lumen is in fluid communication with the barrel chamber. The distal tip of the cannula may be a stopper piercing tip as described hereinabove or a sharp bevel tip suitable for injection such as tip 283.

Referring to FIG. 20, the single-use syringe of the present invention can also be used with a permanently attached cannula 371 having a proximal end 373, a distal end 375 and a lumen therethrough. Barrel 321 includes a tip 328 with a passageway 329 therethrough. The proximal end of the cannula is positioned in the passageway and held permanently to the barrel tip through the use of adhesive 330. There are numerous ways to permanently attach a cannula to a barrel tip such as a press-fit, crimping the barrel tip, and the like, all of which are within the purview of the present invention with the adhesive connection illustrated being merely representative of these many possibilities. The distal tip of the cannula may be a stopper piercing tip as described hereinabove or a sharp bevel tip suitable for injection such as tip 383 as illustrated in FIG. 20.

What is claimed is:

1. An operable single-use syringe comprising:
  a barrel having an inside surface defining a chamber for retaining fluid, an open proximal end and a distal end having a distal wall with a tip extending distally therefrom having a passageway therethrough in fluid communication with said chamber;
  a plunger rod including an elongate body portion defining a longitudinal axis, a proximal end and a distal end, a stopper at said distal end slidably positioned in fluid-tight engagement in said barrel, said body portion extending outwardly from said open proximal end of said barrel, said body portion including two parallel longitudinal slots, at least one of said slots including a plurality of inwardly facing axially spaced discontinuities;
  a locking element positioned in said barrel between said elongate body portion of said plunger rod and said inside surface of said barrel, said locking element having a proximal end, a distal end, a base and two leg members in substantially parallel relationship extending from said base into each of said longitudinal slots, said locking element having an outwardly and proximally directed distal end barb and an outwardly and proximally directed proximal end barb for engaging said inside surface of said barrel to prevent proximal motion of said locking element with respect to said barrel, said legs including at least one outwardly facing deflectable resisting element for engaging said discontinuities on said axial slot for moving said locking element in a distal direction along said inside surface when said plunger rod is advanced in a distal direction and allowing proximal motion of said plunger rod with respect to said locking element for filling said chamber.

2. The single-use syringe of claim 1 wherein locking element includes a second outwardly and proximally directed distal end barb.

3. The single-use syringe of claim 1 wherein said locking element includes a second outwardly and proximally directed proximal end barb.

4. The single-use syringe of claim 1 further including a proximal end barrier at said proximal end of said body portion of said plunger rod for establishing the most proximal position of said locking element on said plunger rod.

5. The single-use syringe of claim 4 wherein said proximal end barrier blocks access to said locking element through said open proximal end of said barrel.

6. The single-use syringe of claim 4 further including a distal end barrier at said distal end of said body portion of said plunger rod establishing the distal-most position of said locking element on said plunger rod.

7. The single-use syringe of claim 1 wherein said at least one outwardly facing deflectable resisting element includes an outwardly facing deflectable resisting element on each leg member.

8. The single-use syringe of claim 7 wherein each of said longitudinal slots includes a plurality of inwardly facing axially spaced discontinuities.

9. The single-use syringe of claim 6 wherein the axial length of said locking element is less than 20% of the distance between said proximal end barrier and said distal end barrier.

10. The single-use syringe of claim 1 wherein said locking element includes a distally directed cutting edge at its distal end capable of cutting into said stopper if excessive proximally-directed force is applied to said plunger rod to overcome the engagement between said locking element and said barrel and remove said plunger rod from said barrel.

11. The single-use syringe of claim 1 wherein said plunger rod and said stopper are integrally formed of the same material.

12. The single-use syringe of claim 1 wherein said locking element is made of sheet metal.

13. The single-use syringe of claim 1 further comprising a needle assembly including a cannula having a proximal end, a distal end and a lumen therethrough, a hub having an open proximal end including a cavity therein, a distal end joined to said proximal end of said cannula so that said lumen is in fluid communication with said cavity, said tip of said barrel engaging said hub so that said lumen is in fluid communication with said chamber.

14. The single-use syringe of claim 1 further comprising a cannula having a proximal end, a distal end and a lumen therethrough wherein said proximal end of said cannula is connected to said tip of said barrel so that said lumen is in fluid communication with said passageway.

15. The single-use syringe of claim 1 further comprising:

an elongate cannula made of thermoplastic material, said cannula having an outside surface, a proximal end, a distal end and a lumen therethrough defining a longitudinal axis, said outside surface at said proximal end including at least one discontinuity, said distal end having a stopper piercing tip; and said barrel being made of thermoplastic material, said tip of said barrel being formed in intimate contact around said proximal end of said cannula engaging said at least one discontinuity so that said lumen is in fluid communication with said chamber, said cannula projecting distally from said distal wall.

16. The single-use syringe of claim 15 wherein said tip of said cannula includes a closed distal end and at least one side aperture in fluid communication with said lumen.

17. The single-use syringe of claim 15 wherein said tip of said cannula includes a planar surface and at an angle with respect to said longitudinal axis.

18. The single-use syringe of claim 15 wherein said cannula projects distally from said distal wall of said barrel for a distance of at least 23 mm (0.9 inch).

19. The single-use syringe of claim 15 wherein the distal end of said cannula has an outside diameter of at least 2 mm (0.08 inch).

20. The single-use syringe of claim 15 wherein said proximal end of said cannula has an outside diameter of at least 2.5 mm (0.1 inch).

21. The single-use syringe of claim 15 wherein said thermoplastic material of said cannula has a flexural modulus of at least 50% greater than the flexural modulus of said thermoplastic material of said barrel.

22. The single-use syringe of claim 15 wherein said cannula is made of polycarbonate.

23. The syringe assembly of claim 15 wherein said barrel is made of polypropylene.

* * * * *